United States Patent [19]

Sasaki et al.

[11] Patent Number: 4,673,756
[45] Date of Patent: Jun. 16, 1987

[54] NEMATIC LIQUID CRYSTALLINE COMPOUNDS

[75] Inventors: Makoto Sasaki, Okegawa; Haruyoshi Sasaki, Kodaira; Hisato Sato, Tokyo, all of Japan

[73] Assignee: Dainippon Ink and Chemicals, Inc., Tokyo, Japan

[21] Appl. No.: 744,978

[22] Filed: Jun. 17, 1985

Related U.S. Application Data

[62] Division of Ser. No. 546,534, Oct. 28, 1983, Pat. No. 4,551,280.

[30] Foreign Application Priority Data

Oct. 30, 1982 [JP] Japan ................... 57-191063
Mar. 18, 1983 [JP] Japan ................... 58-44329
Mar. 18, 1983 [JP] Japan ................... 58-442330

[51] Int. Cl.$^4$ .................. C09K 19/12; G02F 1/13; C07C 121/75
[52] U.S. Cl. ................... 558/416; 252/299.5; 252/299.65; 350/350 R; 558/414
[58] Field of Search ............. 252/299.63, 299.65, 252/299.67, 299.5; 350/350 R, 350 S; 260/465 D; 558/414, 416

[56] References Cited

U.S. PATENT DOCUMENTS

| | | | |
|---|---|---|---|
| 3,925,238 | 12/1975 | Gavrilovic | 252/299.65 |
| 4,017,416 | 4/1977 | Inuka et al. | 252/299.65 |
| 4,198,312 | 4/1980 | Sato et al. | 252/299.67 |
| 4,229,315 | 10/1980 | Krause et al. | 252/299.63 |
| 4,424,371 | 1/1984 | Hsu | 252/299.61 |
| 4,455,261 | 6/1984 | Sasaki et al. | 252/299.67 |
| 4,472,293 | 9/1984 | Sugimori et al. | 252/299.63 |
| 4,490,277 | 12/1984 | Grebenkin et al. | 252/299.63 |
| 4,502,974 | 3/1985 | Sugimori et al. | 252/299.63 |
| 4,542,230 | 9/1985 | Gray et al. | 252/299.65 |
| 4,550,981 | 11/1985 | Petrzilka et al. | 252/299.63 |

FOREIGN PATENT DOCUMENTS

| | | | |
|---|---|---|---|
| 19665 | 12/1980 | European Pat. Off. | 252/299.63 |
| 57-154158 | 9/1982 | Japan | 252/299.63 |
| 58-126838 | 7/1983 | Japan | 252/299.63 |
| 58-126840 | 7/1983 | Japan | 252/299.63 |
| 2063250 | 6/1981 | United Kingdom | 252/299.63 |
| 2063287 | 6/1981 | United Kingdom | 252/299.63 |

OTHER PUBLICATIONS

Osman, M. et al., Mol. Cryst. Liq. Cryst., vol. 82 (Letters), pp. 331-338 (1983).
Gray, G. W. et al., Mol. Cryst. Liq. Cryst., vol. 67, No. 1-4, pp. 1-24 (1981).

*Primary Examiner*—Teddy S. Gron
*Attorney, Agent, or Firm*—Sherman and Shalloway

[57] ABSTRACT

A compound of the general formula

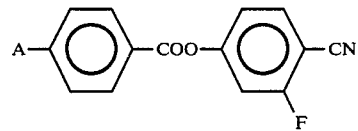

wherein A denotes a substituted ring structure represented by the formula

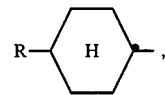

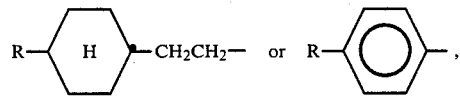

the substituent R denotes a linear alkyl group having 1 to 9 carbon atoms, and the cyclohexane rings are both arranged in a trans(equatorial-equatorial)-form.

4 Claims, 3 Drawing Figures

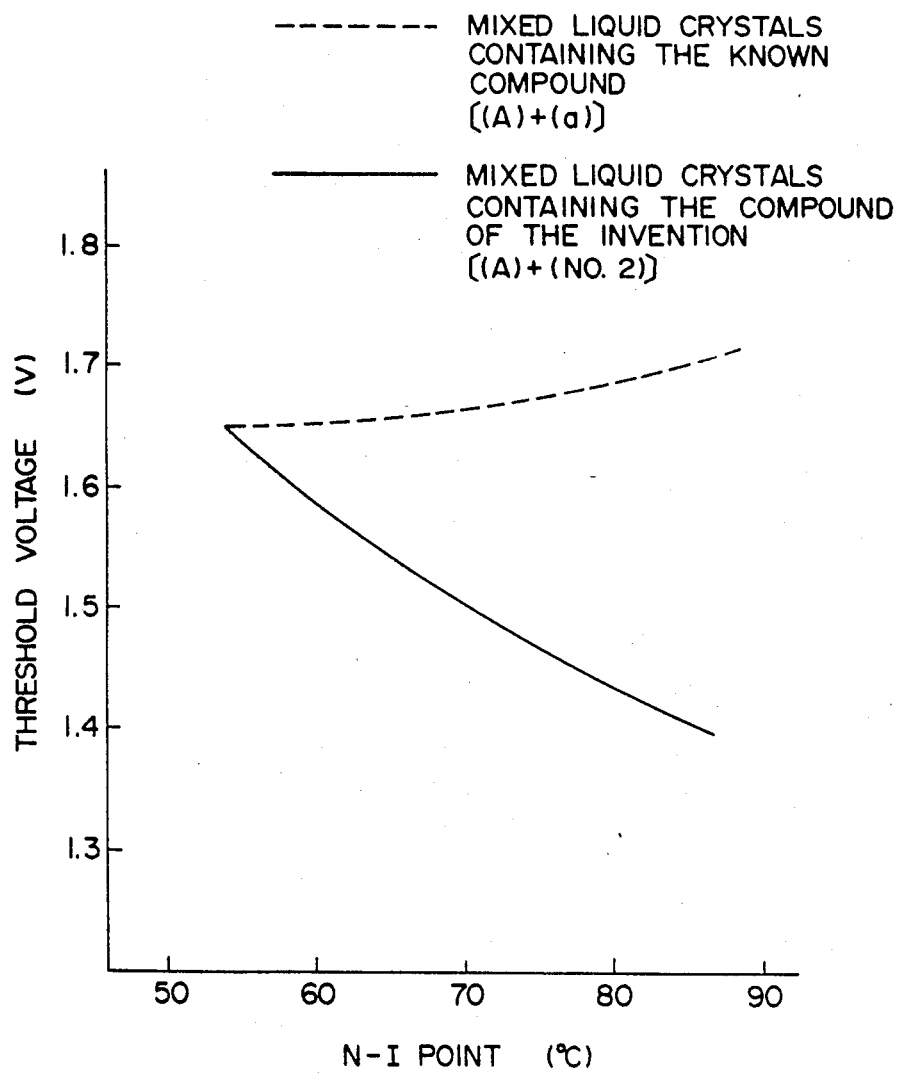

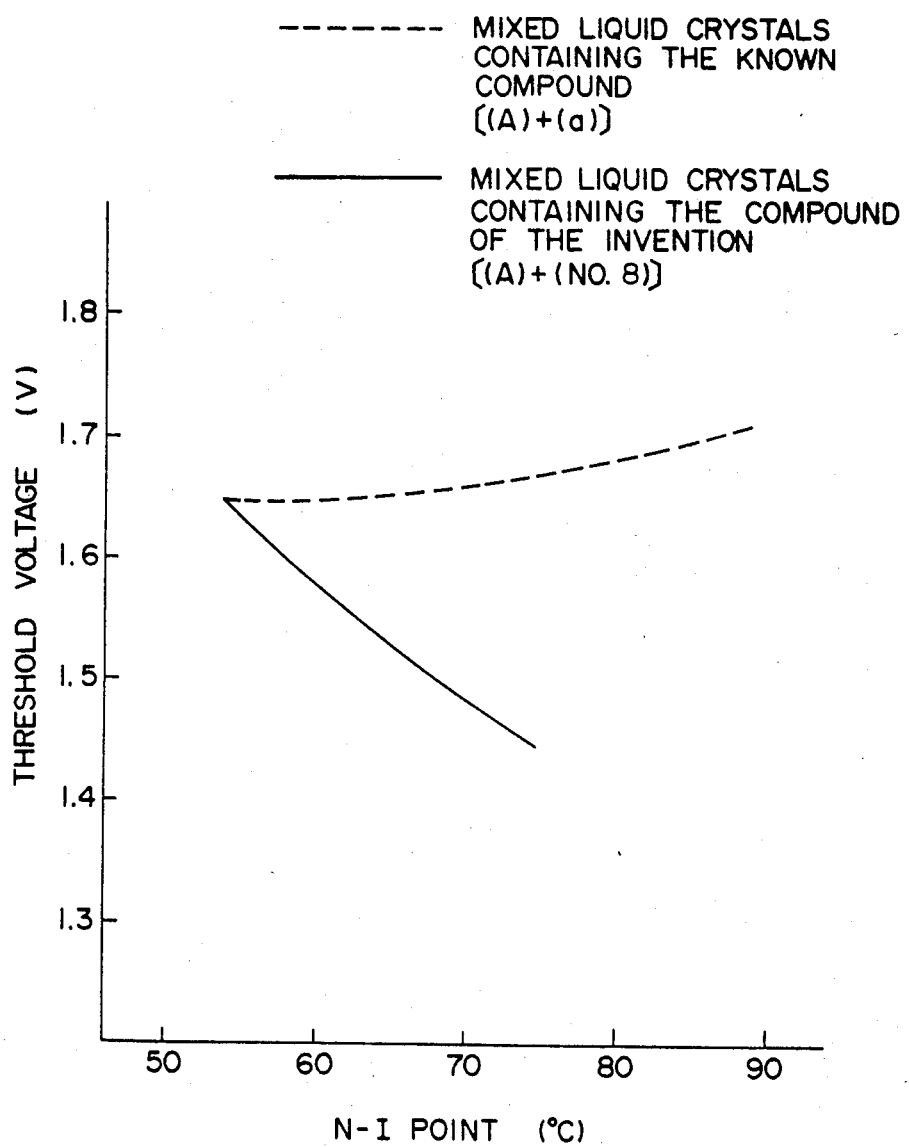

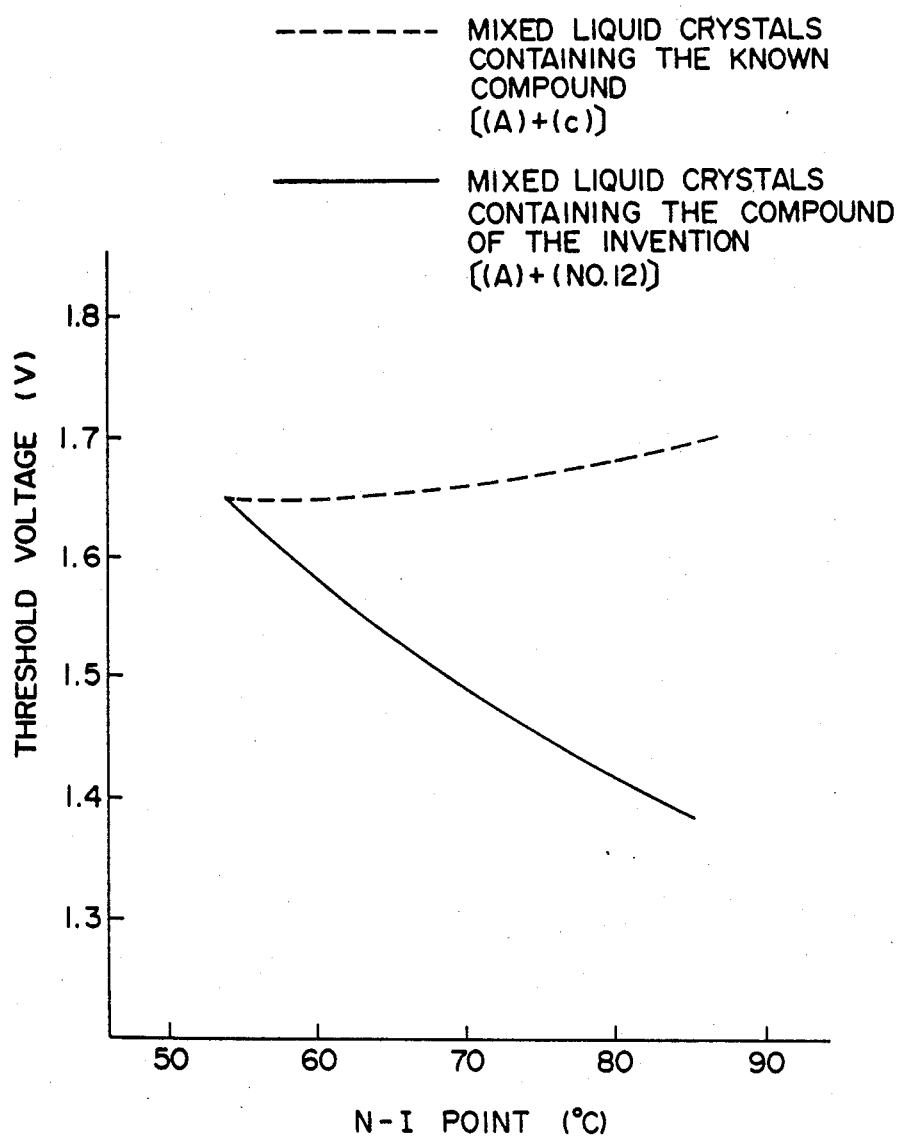

NEMATIC LIQUID CRYSTALLINE COMPOUNDS

This is a division of application Ser. No. 546,534, filed Oct. 28, 1983, now U.S. Pat. No. 4,551,280.

This invention relates to novel nematic liquid crystalline compounds which are 3-fluoro-4-cyanophenol derivatives useful as electro-optical display materials.

The novel nematic liquid crystalline compounds provided by this invention are represented by the following formula

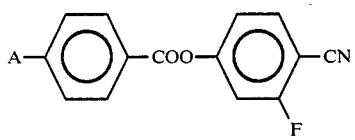

wherein A denotes a substituted ring structure represented by the formula

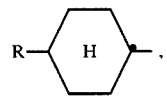

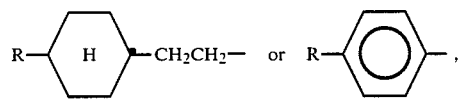

the substituent R denotes a linear alkyl group having 1 to 9 carbon atoms, and the cyclohexane rings are both arranged in a trans(equatorial-equatorial)form.

Typical liquid crystal display cells include, for example, a field effect mode cell proposed by M. Schadt et al. (Applied Physics Letters, 18, 127–128 (1971)], a dynamic scattering mode cell proposed by G. H. Heilmeier [Proceedings of the I.E.E.E., 56, 1162–1171 (1968)], and a guest-host mode cell proposed by G. H. Heilmeir [Applied Physics Letters, 13, 91 (1968)] or D. L. White (Journal of Applied Physics, 45, 4718 (1974)].

Liquid crystalline materials used in the field effect mode cell, above all, a TN mode cell are required to have various properties. A low operating voltage is one of the important properties. In general, the decrease in the operating voltage of liquid crystal display cells corresponds to the decrease in the threshold voltage (Vth) of liquid crystals. The threshold voltage (Vth) of liquid crystals has the following relation between an anisotropy (Δε) of dielectric constant and an elastic constant K.

$$Vth = a\sqrt{\frac{K}{\Delta\epsilon}}$$

A liquid crystalline compound to decrease the threshold voltage (Vth) is, for example, a compound of the following formula having a high anisotropy (Δε).

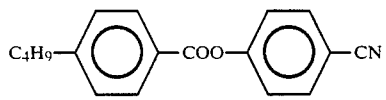

Such a compound has however a low N-I transition temperature, narrowing an operating temperature range of liquid crystals. Moreover, a compound of the following formula having a high N-I transition temperature and a relatively high anisotropy (Δε) increases a threshold voltage (Vth) when mixed with a TN mode liquid crystalline composition because the elastic constant K is also very high.

The compounds of the formula (I) according to this invention are novel compounds with these properties improved. That is, the compounds of the formula (I) are mixed with one or more of other nematic liquid crystalline compounds to increase the N-I transition temperature while decreasing the threshold voltage (Vth). Thus, the use of the compounds of the formula (I) enables the formation of TN mode liquid crystalline compositions wherein the upper limit of the temperature range of the nematic phase is high and the threshold voltage (Vth) is low.

The compounds of the formula (I) in this invention can be produced by the 2-step reaction schematically shown below.

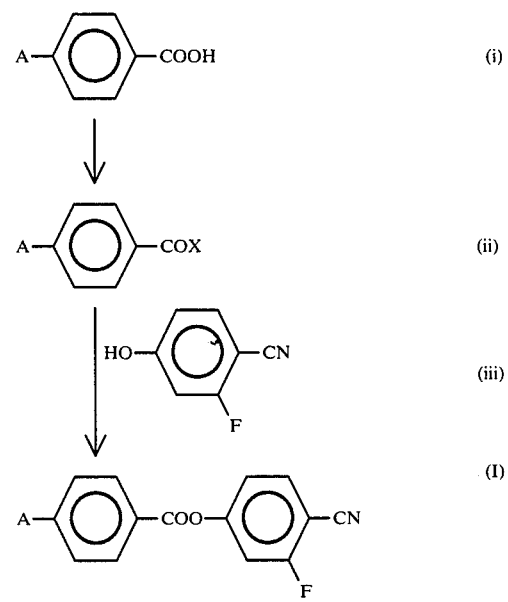

wherein A denotes the aforesaid substituted ring structure.

In the first step, a compound of the formula (i) is reacted with a halogenating agent to provide a compound of the formula (ii) wherein X is a halogen atom. In the compound of the formula (ii), X is preferably a chlorine atom. Thionyl chloride may be used as the halogenating agent. The reaction is carried out at a reflux temperature of the reaction mixture and at normal pressure. It is unnecessary to isolate the compound of the formula (ii) from the mixture formed by the reaction, and it is sufficient to remove excess halogenating agent alone.

In the second step, the crude compound of the formula (ii) afforded in the first step is reacted with a compound of the formula (iii) in an inert organic solvent. Examples of the inert organic solvent include, for example, diethyl ether, tetrahydrofuran, dimethylformamide and benzene. In order to remove hydrogen halides liberated during the reaction from the reaction system, it is advisable to contain basic substances such as pyridine, tertiary amines, etc. in said inert organic solvent. The reaction is carried out at temperatures ranging from room temperature to a reflux temperature of the reaction mixture and at normal pressure. The final compound of the formula (I) can be isolated by subjecting the reaction product to a series of purifying treatments such as solvent extraction, water-washing, drying, recrystallization, and so forth.

The transition temperatures of the typical compounds represented by the formula (I) which are produced as above are shown in Table 1. In table 1, C represents a crystalline phase; N, a nematic phase; and I, an isotropic liquid phase.

TABLE 1

A—⌬—COO—⌬—CN
                    |
                    F

| Compound No. | A | C→N | N⇌I |
|---|---|---|---|
| 1 | $C_2H_5$—⟨H⟩— | 88 | 172 |
| 2 | n-$C_3H_7$—⟨H⟩— | 101 | 203 |
| 3 | n-$C_4H_9$—⟨H⟩— | 81 | 192 |
| 4 | n-$C_5H_{11}$—⟨H⟩— | 91 | 195 |
| 5 | n-$C_6H_{13}$—⟨H⟩— | 85 | 178 |
| 6 | n-$C_7H_{15}$—⟨H⟩— | 80 | 167 |
| 7 | $C_2H_5$—⟨H⟩—$CH_2CH_2$— | 64 | 157 |
| 8 | n-$C_3H_7$—⟨H⟩—$CH_2CH_2$— | 60 | 160 |
| 9 | n-$C_4H_9$—⟨H⟩—$CH_2CH_2$— | 57 | 148 |
| 10 | n-$C_5H_{11}$—⟨H⟩—$CH_2CH_2$— | 53 | 142 |
| 11 | $C_2H_5$—⌬— | 129 | 206 |
| 12 | n-$C_3H_7$—⌬— | 104 | 207 |
| 13 | n-$C_4H_9$—⌬— | 92 | 197 |

TABLE 1-continued

A—⌬—COO—⌬—CN
                    |
                    F

| Compound No. | A | C→N | N⇌I |
|---|---|---|---|
| 14 | $C_5H_{11}$—⌬— | 84 | 191 |

The compounds of the formula (I) in accordance with this invention are nematic liquid crystalline compounds having a strong positive dielectric anisotropy and therefore can be used, for example, as materials for field effect mode display cells in the form of mixtures with other nematic liquid crystalline compounds having a negative or weak positive dielectric anisotropy or other nematic liquid crystalline compounds having a strong positive dielectric anisotropy.

Typical examples of nematic liquid crystalline compounds which can preferably be used in admixture with the compounds of the formula (I) include phenyl 4,4'-substituted benzoates, phenyl 4,4'-substituted cyclohexanecarboxylates, biphenyl 4,4'-substituted cyclohexanecarboxylates, 4'-substituted phenyl 4(4-substituted cyclohexanecarbonyloxy)benzoates, 4'-substituted phenyl 4(4-substituted cyclohexyl)benzoates, 4'-substituted cyclohexyl 4(4-substituted cyclohexyl)benzoates, 4,4'-biphenyl, 4,4'-phenylcyclohexane, 4,4'-substituted terphenyl, 4,4'-biphenylcyclohexane, and 2(4'-substituted phenyl)-5-substituted pyrimidine.

Table 2 indicates the N-I points and threshold voltages (Vth) measured for mixed liquid crystals composed of 80% by weight of matrix liquid crystals (A) now in widespread use as a nematic liquid crystalline material having excellent characteristics for time multiplex drive and 20% by weight of compounds Nos. 1 to 14 of the formula (I) respectively indicated in Table 1. The same table also illustrates the N-I point and threshold voltage measured for the matrix liquid crystals (A) for comparison.

The matrix liquid crystals (A) comprises

20% by weight of n-$C_3H_7$—⟨H⟩—⌬—CN,

16% by weight of n-$C_5H_{11}$—⟨H⟩—⌬—CN,

16% by weight of n-$C_7H_{15}$—⟨H⟩—⌬—CN,

8% by weight of n-$C_3H_7$—⟨H⟩—COO—⌬—$OC_2H_5$,

8% by weight of n-$C_3H_7$—⟨H⟩—COO—⌬—O-n-$C_4H_9$,

8% by weight of n-$C_4H_9$—⟨H⟩—COO—⌬—$OCH_3$,

-continued

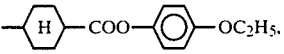
8% by weight of n-C$_4$H$_9$—H—COO—○—OC$_2$H$_5$,

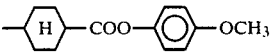
8% by weight of n-C$_5$H$_{11}$—H—COO—○—OCH$_3$ and

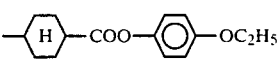
8% by weight of n-C$_5$H$_{11}$—H—COO—○—OC$_2$H$_5$.

TABLE 2

|  | N-I point (°C.) | Threshold voltage (Vth) (V) |
| --- | --- | --- |
| (A) | 54.0 | 1.65 |
| (A) + (No. 1) | 76.2 | 1.41 |
| (A) + (No. 2) | 82.4 | 1.42 |
| (A) + (No. 3) | 80.2 | 1.43 |
| (A) + (No. 4) | 80.8 | 1.44 |
| (A) + (No. 5) | 77.4 | 1.46 |
| (A) + (No. 6) | 75.2 | 1.48 |
| (A) + (No. 7) | 72.6 | 1.46 |
| (A) + (No. 8) | 73.0 | 1.46 |
| (A) + (No. 9) | 71.6 | 1.49 |
| (A) + (No. 10) | 71.2 | 1.49 |
| (A) + (No. 11) | 82.9 | 1.40 |
| (A) + (No. 12) | 82.8 | 1.40 |
| (A) + (No. 13) | 81.9 | 1.43 |
| (A) + (No. 14) | 81.2 | 1.44 |

From the data shown in Table 2 above, it follows that the compounds of the formula (I) can decrease the threshold voltage (Vth) of mixed liquid crystals and besides increase the N-I point thereof. Thus, the high practical value of the compounds of the formula (I) resides in that the mixed liquid crystals having the low threshold voltage (Vth) and high N-I points can be obtained.

The superiority provided by the compounds of this invention is illustrated by the following Comparative Examples.

FIGS. 1, 2 and 3 attached hereto are graphs that compare properties of mixed liquid crystals prepared in the Comparative Examples 1, 2 and 3.

COMPARATIVE EXAMPLE 1

A known compound of the following formula

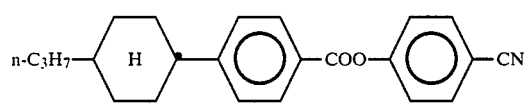
(a)
n-C$_3$H$_7$—H—○—COO—○—CN which has a chemical structure similar to the compound of the formula (I) in accordance with this invention and is widely used in order to increase the N-I point of mixed liquid crystals was mixed in various proportions with the matrix liquid crystals (A) described above to provide a large number of mixed liquid crystals containing the known compound.

Likewise, one compound of this invention represented by the following formula

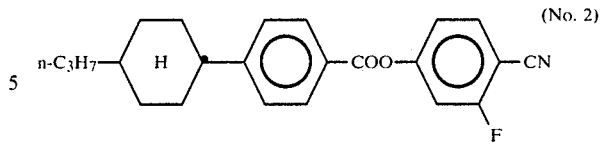
(No. 2)
n-C$_3$H$_7$—H—○—COO—○—CN
                              F was mixed in various proportions with the matrix liquid crystals (A) to provide a large number of mixed liquid crystals containing the compound of this invention.

With respect to the thus obtained mixed liquid crystals, the threshold voltage (Vth) and N-I point were measured and the resulting data were plotted in FIG. 1.

COMPARATIVE EXAMPLE 2

A known compound of the following formula

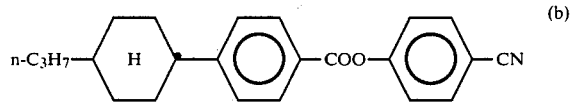
(b)
n-C$_3$H$_7$—H—○—COO—○—CN which has a chemical structure similar to the compound of the formula (I) in accordance with this invention and is widely used in order to increase the N-I point of mixed liquid crystals was mixed in various proportions with the matrix liquid crystals (A) described above to provide a large number of mixed liquid crystals containing the known compound.

Likewise, one compound of this invention represented by the following formula

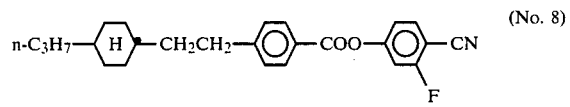
(No. 8)
n-C$_3$H$_7$—H—CH$_2$CH$_2$—○—COO—○—CN
                                          F was mixed in various proportions with the matrix liquid crystals (A) to provide a large number of mixed liquid crystals containing the compound of this invention.

With respect to the matrix liquid crystals (A) and mixed liquid crystals thus obtained, the threshold voltage (Vth) and N-I point were measured and the resulting data were plotted in FIG. 2.

COMPARATIVE EXAMPLE 3

A known compound of the following formula

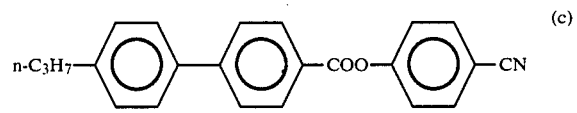
(c)
n-C$_3$H$_7$—○—○—COO—○—CN which has a chemical structure similar to the compound of the formula (I) in accordance with this invention and is widely used in order to increase the N-I point of mixed liquid crystals was mixed in various proportions with the matrix liquid crystals (A) described above to afford a large number of mixed liquid crystals containing the known compound.

Likewise, one compound of this invention represented by the following formula

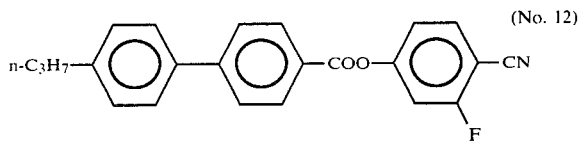
(No. 12)

was mixed in various proportions with the matrix liquid crystals (A) to afford a large number of mixed liquid crystals containing the compound of this invention.

With respect to the matrix liquid crystals and mixed liquid crystals thus obtained, the threshold voltage (Vth) and N-I point were measured and the resulting data were plotted in FIG. 3.

From the facts indicated in FIGS. 1 to 3, it can be seen that in the mixed liquid crystals containing the typical known compounds similar in chemical structure to those of this invention, as the N-I point increases, the threshold voltage increases, whereas in the mixed liquid crystals containing the compounds of the formula (I) in accordance with this invention, as the N-I point increases, the threshold voltage decreases.

The following Examples illustrate production of the compounds in this invention specifically.

EXAMPLE 1

Thionyl chloride (30 cc, 0.0052 mole) was added to 1.2 g (0.0052 mole) of a compound of the following formula.

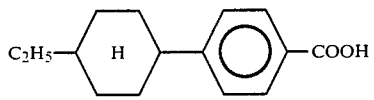

The mixture was reacted for 30 minutes under reflux and excess thionyl chloride was then distilled off. Subsequently, 0.70 g (0.0052 mole) of the following formula

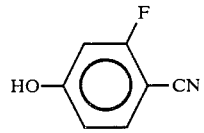

was added to the resulting reaction product, and 30 cc of toluene and 1 g of pyridine were further added. They were reacted for 30 minutes under reflux. The reaction liquid was then washed with 1% hydrochloric acid and water to render said liquid neutral. Toluene was then distilled off from the reaction liquid. The resulting reaction product was recrystallized from ethanol to afford 1.0 g (0.0029 mole) of a compound of the following formula.

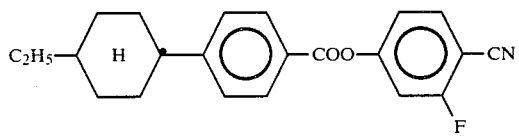

Yield: 54%
Transition temperatures:
  88° C. (C→N)
  172° C. (N⇌I)

EXAMPLE 2

A compound of the following formula was produced as in Example 1.

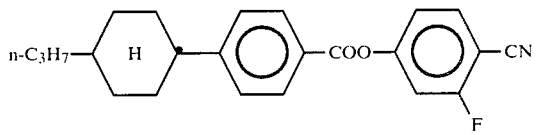

Yield: 70%
Transition temperatures:
  101° C. (C→N)
  203° C. (N⇌I)

EXAMPLE 3

A compound of the following formula was produced as in Example 1.

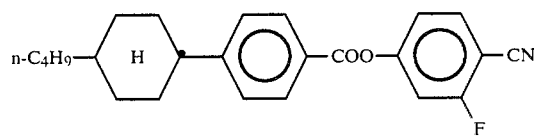

Yield: 72%
Transition temperatures:
  81° C. (C→N)
  192° C. (N⇌I)

EXAMPLE 4

A compound of the following formula was produced as in Example 1.

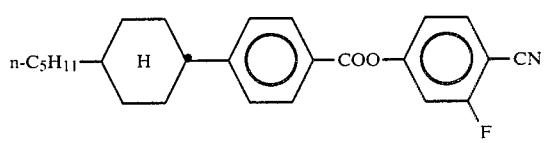

Yield: 69%
Transition temperatures:
  91° C. (C→N)
  195° C. (N⇌I)

EXAMPLE 5

A compound of the following formula was produced as in Example 1.

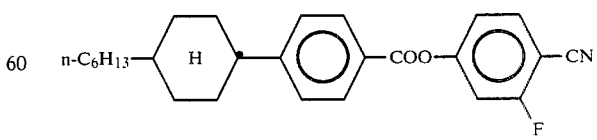

Yield: 70%
Transition temperatures:
  85° C. (C→N)
  178° C. (N⇌I)

EXAMPLE 6

A compound of the following formula was produced as in Example 1.

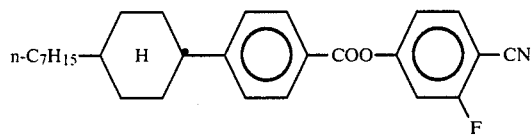

Yield: 74%
Transition temperatures:
  80° C. (C→N)
  167° C. (N⇌I)

EXAMPLE 7

Thionyl chloride (30 cc) was added to 0.89 g (0.00342 mole) of a compound of the following formula

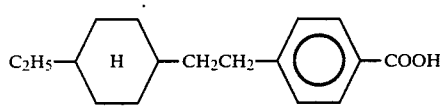

and the mixture was reacted for 30 minutes under reflux, followed by distilling off excess thionyl chloride. To the resulting reaction product were then added 0.47 g (0.00342 mole) of a compound of the following formula

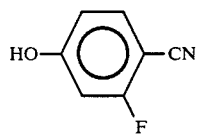

30 cc of toluene and 1 g of pyridine. They were reacted under reflux. The reaction liquid was then washed with 1% hydrochloric acid and water to render said liquid neutral. Subsequently, toluene was distilled off from the reaction liquid. The resulting reaction product was recrystallized from ethanol to obtain 0.89 g (0.00236 mole) of a compound of the following formula.

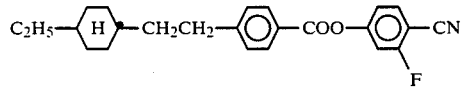

EXAMPLE 8

A compound of the following formula was produced as in Example 7.

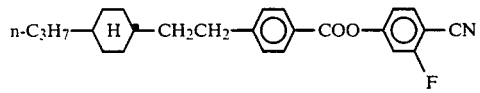

Yield: 75%
Transition temperatures:
  64° C. (C→N)
  157° C. (N⇌I)

EXAMPLE 9

A compound of the following formula was produced as in Example 7.

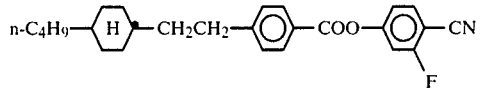

Yield: 70%
Transition temperatures:
  57° C. (C→N)
  148° C. (N⇌I)

EXAMPLE 10

A compound of the following formula was produced as in Example 7.

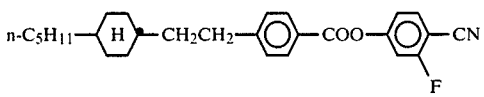

Yield: 65%
Transition temperatures:
  53° C. (C→N)
  142° C. (N⇌I)

EXAMPLE 11

Thionyl chloride (50 cc) was added to 2.26 g (0.01 mole) of a compound of the following formula

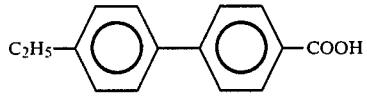

and the mixture was reacted for 30 minutes under reflux, followed by distilling off excess thionyl chloride. Subsequently, to the resulting reaction product were added 1.37 g (0.01 mole) of a compound of the following formula

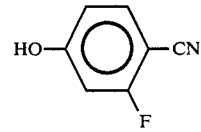

50 cc of toluene and 2 g of pyridine. They were reacted under reflux. The reaction liquid was washed with 1% hydrochloric acid and water to render said liquid neutral, and toluene was then distilled off from the reaction liquid. The resulting reaction product was recrystallized from ethanol to obtain 2.8 g (0.008 mole) of a compound of the following formula.

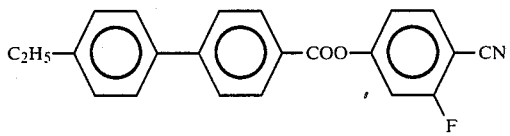

Yield: 80%

Transition temperatures:
 129° C. (C→N)
 206° C. (N⇌I)

EXAMPLE 12

A compound of the following formula was produced as in Example 11.

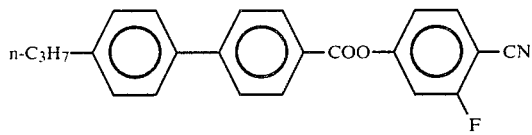

Yield: 75%
Transition temperatures:
 104° C. (C→N)
 207° C. (N⇌I)

EXAMPLE 13

A compound of the following formula was produced as in Example 11.

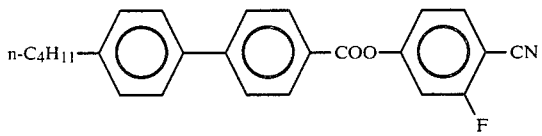

Yield: 68%
Transition temperatures:
 92° C. (C→N)
 197° C. (N⇌I)

EXAMPLE 14

A compound of the following formula was produced as in Example 11.

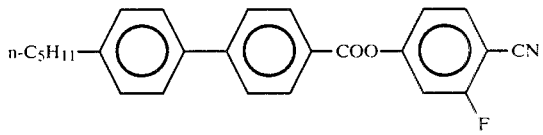

Yield: 72%
Transition temperatures:
 84° C. (C→N)
 191° C. (N⇌I)

What is claimed is:
1. A compound of the general formula

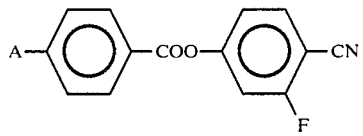

wherein A denotes a substituted ring structure represented by the formula

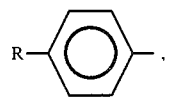

the substituent R denotes a linear alkyl group having 1 to 9 carbon atoms.

2. The compound of the general formula as set forth in claim 1 wherein R is a linear alkyl group having from 2 to 5 carbon atoms.

3. The compound of the general formula as set forth in claim 1 wherein R is $C_3H_7$.

4. The compound of the general formula of claim 1 wherein R is $C_5H_{11}$.

* * * * *

UNITED STATES PATENT AND TRADEMARK OFFICE
CERTIFICATE OF CORRECTION

PATENT NO. : 4,673,756

DATED : June 16, 1987

INVENTOR(S) : MAKOTO SASAKI, ET AL.

It is certified that error appears in the above-identified patent and that said Letters Patent is hereby corrected as shown below:

Under "Foreign Application Priority Data", the third Japanese application, delete "58-442330", insert --58-44330--.

Signed and Sealed this

Tenth Day of November, 1987

Attest:

DONALD J. QUIGG

Attesting Officer

Commissioner of Patents and Trademarks